United States Patent [19]

Gerzon

[11] 4,415,590
[45] Nov. 15, 1983

[54] HERPES TREATMENT

[75] Inventor: Koert Gerzon, Indianapolis, Ind.

[73] Assignee: BetaMED Pharmaceuticals, Inc., Indianapolis, Ind.

[21] Appl. No.: 372,176

[22] Filed: Apr. 26, 1982

[51] Int. Cl.$^3$ ............................................ A61K 31/195
[52] U.S. Cl. .................................................... 424/319
[58] Field of Search ........................................ 424/319

[56] References Cited
PUBLICATIONS

Chemical Abstracts 58:1319e (1963).
The Merck Index, 9th ed., Merck & Co., Inc., Rahway, N.J., 1976, p. 733 (No. 5456).

Primary Examiner—Jerome D. Goldberg
Attorney, Agent, or Firm—Barnes & Thornburg

[57] ABSTRACT

L-lysine L-glutamate, when injected intradermally in the form of a sterile aqueous solution, or applied topically in the form of a cream, ointment, or lotion, is effective for treating and relieving the symptons of Herpes simplex I and II infections.

7 Claims, No Drawings

HERPES TREATMENT

The present invention relates to viral infections of the herpes type, including in particular Herpes simplex I and Herpes simplex II. More particularly, it relates to a method and means for the alleviation and control of such infections.

Man himself is the reservoir of herpes virus hominis. It has been reported in one study that antibodies to herpes virus were found in 30–37% of college students, 62% of private patients, and more than 80% of ward service patients. Although the virus is carried as a latent infection in a majority of individuals, in others an acute exacerbation of the activated virus takes place in a variety of forms and can be precipitated by a variety of factors, including traumatic factors such as sunlight, menstruation, and family upsets. Cold sores or fever blisters are thought to be caused by Herpes simplex I, whereas the Herpes simplex II is thought to be the agent in genital herpes infections.

A striking feature of herpes infections is their occurence in patients known to have an appreciable titer of herpes antibodies. The presence of antibodies is thus not a guarantee of protection agaist acute outbreaks.

The route of infection of herpes virus appears to be by direct contact such as may occur between sexual partners, mother and child, even patient and dentist.

Oral herpes disease may take the form of recurrent labial lesions. Some patients have severe oral lesions causing considerable difficulty in eating. It has been estimated that up to a third of the population have recurrent episodes of oral infection and that over half of these patients have more than one attack each year.

Viruses of the herpes group cause severe disease in patients who are immunologically deficient, and particularly in patients being treated for cancer with drugs having immunosuppressive properties.

Ocular herpes and herpes encephalitis are additional forms of infections with herpes virus requiring continued and intensive medical attention.

Genital herpes, which had an estimated incidence of 100,000 cases in the U.S. in 1973, by 1980 had been estimated to affect 30% of the sexually active population. The problem of herpes infections is thus a serious and growing one.

Among the more active agents heretofore employed for the treatment of herpes virus infections are a group of nucleoside analogs. These substances undergo conversion in vivo to an activated form, e.g., phosphate or triphosphate, by the action of enzymes present in the infected cell, and achieve their action by interference with nucleoside metabolism in the infected cell. Among the nucleoside analogs that have been used are the following:

Idoxuridine(5-iodo-2'-deoxyuridine)
Trifluoromethylthymidine(5-trifluoromethyl-2'-deoxyuridine)
Ara-C(1-$\beta$-D-arabinofuranosylcytosine)
Ara-A(9-$\beta$-D-arabinofuranosyladenine)
1-(2'-deoxy-2'-fluoro-$\beta$-D-arabinofuranosyl)-5-iodocytosine
E-5-(2-bromovinyl)-2'-deoxyuridine
Acyclovir(9-(2-hydroxyethyoxymethyl)guanine)

The last agent, acyclovir, developed at Wellcome Research Laboratories, is reported to be nearing approval by the Food and Drug Administration for topical use in treating herpes.

A second class of antiherpetic agents, phosphonoacetate and phosphonoformate, do not require enzymatic activation and appear to act upon herpes virus DNA polymerase.

A third type of antiherpetic agent described in the literature is the amino acid lysine, a component of the proteins occurring in natural foodstuffs. Tankersley (*J. Bact.*, 87, 609–613, 1964) observed that arginine, when added to cell cultures harboring herpes-infected cells, aided in the replication of the virus, while lysine actually depressed viral replication in these cultures. On the basis of these observations, Kagan recommended that lysine hydrochloride be evaluated in patients with Herpes simplex infections (*Lancet*, Jan. 26, 1974, p. 137). Milman and associates (*Lancet*, Oct. 28, 1978, p. 942) subsequently reported on the failure of lysine hydrochloride treatment in patients with recurrent Herpes simplex labialis. In the Milman study, it was concluded that a dose of 500 mg of lysine hydrochloride given orally in a tablet twice a day—the maximum size that could be given without discomfort—was inadequate to register a positive therapeutic effect.

Griffith, Norris, and Kagan (*Dermatologica*, 156, 257–267, 1978) reported on a multicentered study of oral lysine monohydrochloride in treating patients with recurring Herpes simplex infections. Some degree of acceleration of recovery was observed, as well as suppression of recurrences. Doses given ranged from 312 mg of lysine hydrochloride daily to 1,200 mg daily in single or multiple doses. As patients often experienced return of lesions within one to four weeks after stopping medication, it was concluded that the results should be interpreted as suppressive rather than curative. When the amount of lysine ingested was cut back in an effort to establish a maintenance level, some patients noted a "break through" phenomenon. Consequently, although a positive effect was observed, the establishment of a maintenance dosage was not achieved. It appears, therefore, that lysine, as heretofore employed, has given encouraging results in the treatment of herpes infections, but is less than the whole answer, particularly in that it cannot be said to effect a cure, and has been unsuccessful in preventing recurrences.

It is an object of this invention to provide an effective treatment of herpes and of herpes-like infections.

Another object is to prevent the recurrence of herpes infections.

A further object is to minimize side effects in the treatment of herpes infections.

Other objects will be apparent from the following description and claims.

I have discovered that the L-glutamic acid salt of L-lysine, described in Emmick U.S. Pat. No. 2,556,907 (1951) and in Rogers U.S. Pat. No. 2,657,230 (1953), is effective in the treatment of Herpes simplex I and II infections. For maximum effectiveness, the salt is preferably administered by intradermal injection in the form of a sterile aqueous solution, e.g., in water, in water buffered to pH 7.4–7.6 with sodium bicarbonate or sodium dihydrogen phosphatedisodium hydrogen phosphate, or in normal saline. It is also effective in the treatment of lesions of the lips, mouth, gums, and genitalia when applied in the form of a cream, ointment, or lotion, using in each case a base of the types well known in the art.

My choice of L-glutamic acid to form a salt with L-lysine was prompted by the fact that it is an amino acid, like lysine, of natural occurrence, which I deemed less likely to produce side effects of toxic or otherwise harmful nature. It was therefore quite unexpected to find that similar results were not obtained with a mixture of L-lysine and L-glutamic acid, or with the L-aspartic acid salt of L-lysine, or with ornithine hydrochloride alone, or with L-glutamic acid alone. I have also confirmed the indications in the prior art that L-lysine hydrochloride alone is relatively less effective.

In accordance with one embodiment of the invention, L-lysine L-glutamate in finely divided form (particle size smaller than 200 mesh) is commingled and vigorously agitated with an aqueous sodium bicarbonate buffer solution (pH 7.5) to form a solution containing around 1 to 2 mg of the L-lysine L-glutamate per milliliter. The solution is sterilized by filtration through a Beckman microfilter, aliquots are collected in sterile ampoules, the contents are lyophilized, and the ampoules are stoppered.

When needed for injection, the lyophilized solids are reconstituted to the original concentration with sterile bicarbonate solution containing a small amount of a suitable disinfectant (e.g., benzyl alcohol) and administered to the patient intradermally once a week for a period of three weeks at a weekly dosage preferably around 0.5 to 2 mg.

In another embodiment, L-lysine L-glutamate is administered in an analogous way as a sterile solution in a phosphate buffer, pH 7.4–7.6.

In a further embodiment, L-lysine L-glutamate is similarly administered in sterile saline solution.

It will be apparent that other aqueous solutions may also be used, including water itself; but to promote stability of the solution, it is preferred to use an aqueous tissue-compatible buffer solution.

For topical application, the L-lysine L-glutamate is preferably dispersed in the form of a fine powder in a conventional cream base at a concentation between about 0.5 and about 5% by weight, e.g., around 2%. The cream is applied liberally to the affected parts and rubbed gently into the tissues. Applications may be made one, two, or more times a day. The cream form is generally best adapted for topical applications, particularly intrabuccally and intravaginally. Ointments, or (less desirably) lotions, may also be used, prepared with bases well known in the art.

Because L-lysine L-glutamate is well tolerated by the body tissues, its concentration in the injection liquid is not limited by toxicity but, at the lower range of concentrations, by the maximum tolerable volume for injection and, at the upper range, by the necessity to maintain fluidity for injection. The concentration may thus range from about 0.5 mg/ml to about 5 mg/ml and over. In the same way, the volume for injection may range from around 0.1 ml for a small child to a typical range of 0.5 to 5 milliliters for adults of increasing size. The total weekly dose can suitably be from about 0.5 to about 5 mg.

L-lysine L-glutamate is available from Sigma Chemical Company, St. Louis, as Product No. 8876. It can be prepared in a variety of known ways, e.g., as described in Rogers U.S. Pat. No. 2,657,230 (1963), either directly from L-lysine, or in the course of the resolution of DL-lysine with L-glutamic acid.

The following examples will more fully illustrate the invention.

EXAMPLE 1

L-lysine L-glutamate is prepared according to the following procedure. L-lysine (36.5 g) is dissolved in 99 ml of water and to the solution is added L-glutamic acid (36.5 g). The mixture is stirred at room temperature until dissolved, then heated to 60° C. One gram of L-lysine L-glutamate is finely ground in contact with methanol and added to the reaction mixture as seed, together with 30.4 g 28% ammonium hydroxide and 469 g of methanol. Stirring is continued at 60° C. for one hour, during which time the L-lysine L-glutamate crystallizes as the monohydrate. The solids are filtered off and washed successively with 250 ml portions of aqueous 80 vol-% methanol, aqueous 90 vol-% methanol, and pure methanol, precautions being taken to protect the crystals from atmospheric moisture. The washed crystals are dried and stored out of contact with the atmosphere.

The salt thus obtained, when dissolved in aqueous sodium bicarbonate buffer, pH 7.4, to a concentration of 1 mg/ml and injected intradermally once a week at a dosage of 1 mg, is effective to relieve and control herpes infections, both Herpes simplex I and II, within a period of three weeks.

EXAMPLE 2

L-lysine L-glutamate (1 g) is mulled with a conventional cream base (99 g) composed of glycerol, glyceryl monostearate, Polysorbate 80, cetyl alcohol, mineral oil, lanolin, propylene glycol, water, Methylparaben, and Propylparaben to provide a cream of smooth texture and flowable consistency. The resulting 1% cream, when gently applied to herpes lesions, is effective in relieving them in a period of one to three weeks.

EXAMPLE 3

L-lysine L-glutamate (2 g) is blended with a conventional ointment base (98 g) having the following composition:
Methylparaben—0.025 g
Propylparaben—0.015 g
Sodium lauryl sulfate—1 g
Propylene glycol—12 g
Stearyl alcohol—25 g
White petrolatum—25 g
Water—37 g The stearyl alcohol and the white petrolatum are melted together on a steam bath and warmed to about 75° C. The other ingredients, including the L-lysine L-glutamate, are dissolved in the water warmed to 75° C., and added to the stearyl alcohol-white petrolatum mix. The total mixture is then stirred and cooled until it congeals. The completed ointment is effective, when applied topically, in controlling herpes lesions.

EXAMPLE 4

L-lysine L-glutamate (1 g) is dissolved in a conventional lotion base (100 g) having the following composition:
Triethanolamine—0.5 g
Oleic acid—2.5 g
Water—97 g The resulting lotion is conveniently applied to larger areas of the body, and is effective in treating the lesions of Herpes simplex I and II.

While I have described my invention with reference to certain specific embodiments thereof, it is to be understood that such embodiments are illustrative only. Numerous modifications and equivalents will be apparent to those skilled in the art without departing from the spirit of the invention.

I claim:

1. A method for the control of herpes virus infections in man which comprises contacting the herpes lesions, topically or by injection, with a dose of L-lysine L-glutamate effective to control the said infections.

2. A method as in claim 1 wherein the herpes lesions are treated topically with a cream containing an effective dosage of L-lysine L-glutamate.

3. A method as in claim 1 wherein the herpes lesions are treated topically with an ointment containing an effective dosage of L-lysine L-glutamate.

4. A method as in claim 1 wherein the herpes lesions are treated topically with a lotion containing an effective dosage of L-lysine L-glutamate.

5. A method as in claim 1 wherein an effective dose of L-lysine L-glutamate in a sterile aqueous buffer is injected intradermally into a herpes-infected patient.

6. A method as in claim 5 wherein said effective dose is between about 0.5 and about 5 milligrams.

7. A method as in claim 5 wherein said L-lysine L-glutamate is injected at a dosage of around 0.5 to 2 mg once a week for a period of at least three weeks.

* * * * *